United States Patent
Kim et al.

(10) Patent No.: US 9,483,617 B2
(45) Date of Patent: Nov. 1, 2016

(54) SYSTEM AND METHOD FOR EVALUATING LASER TREATMENT

(71) Applicant: Seoul National University R&DB FOUNDATION, Seoul (KR)

(72) Inventors: Sungwan Kim, Seoul (KR); Seung Woo Noh, Busan (KR); Hyoung Woo Lim, Seoul (KR); Chi Yul Yoon, Seoul (KR); Youdan Kim, Seoul (KR); Jin Ho Chung, Seoul (KR); Hee Chan Kim, Seoul (KR); Woo Seok Koh, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 61 days.

(21) Appl. No.: 14/681,120

(22) Filed: Apr. 8, 2015

(65) Prior Publication Data
US 2015/0287190 A1    Oct. 8, 2015

(30) Foreign Application Priority Data

Apr. 8, 2014   (KR) .................. 10-2014-0042096
Aug. 9, 2014   (KR) .................. 10-2014-0102693

(51) Int. Cl.
*G06K 9/00*      (2006.01)
*G06F 19/00*     (2011.01)

(52) U.S. Cl.
CPC ..... *G06F 19/3406* (2013.01); *A61B 2034/104* (2016.02)

(58) Field of Classification Search
None
See application file for complete search history.

(56) References Cited

U.S. PATENT DOCUMENTS

| | | | |
|---|---|---|---|
| 8,824,779 B1* | 9/2014 | Smyth | G06K 9/0061 382/100 |
| 2002/0097504 A1* | 7/2002 | Kitamura | G02B 9/12 359/719 |
| 2004/0016930 A1* | 1/2004 | Yoshida | H01L 22/32 257/79 |
| 2013/0237973 A1 | 9/2013 | Kim et al. | |

FOREIGN PATENT DOCUMENTS

| | | |
|---|---|---|
| JP | H08-299353 A | 11/1996 |
| KR | 10-2008-0108474 A | 12/2008 |
| KR | 10-1219682 B1 | 1/2013 |

* cited by examiner

*Primary Examiner* — Hadi Akhavannik
(74) *Attorney, Agent, or Firm* — Park, Kim & Suh, LLC

(57) ABSTRACT

Provided is a system and method for evaluating laser treatment, for converting the attribute of a laser beam and numerically evaluating proficiency of a laser treatment operator by processing data obtained by photographing the converted laser beam so as to use the evaluated data as training data. The laser treatment evaluating system includes an attenuation unit for attenuating intensity of a laser beam transmitted through a transmissive plate, a camera for photographing the laser beam transmitted through the attenuation unit, and an image data processing apparatus connected to the camera, for processing an image captured by the camera, tracking a trajectory of a laser beam on the transmissive plate, and calculating a distribution state of spots on which the laser beam on the transmissive plate is emitted.

10 Claims, 5 Drawing Sheets

SYSTEM AND METHOD FOR EVALUATING LASER TREATMENT

CROSS-REFERENCE TO RELATED APPLICATIONS

This application claims priority to Korean Patent Application Nos. 10-2014-0042096 filed on Apr. 8, 2014 and 10-2014-0102693 filed on Aug. 9, 2014, which are all hereby incorporated by reference in their entirety.

BACKGROUND OF THE INVENTION

1. Field of the Invention

The present invention relate to a system and method for evaluating laser treatment, and more particularly, a system and method for evaluating laser treatment, for converting the attribute of a laser beam and numerically evaluating proficiency of a laser treatment operator by processing data obtained by photographing the converted laser beam so as to use the evaluated data as training data.

2. Description of the Related Art

Today it is been about 20 years since Food and Drug Administration (FDA) has first authorized a clinic laser and an aesthetic laser treatment has been used as an example of successful application of a laser in a medical field.

Korean Patent Publication No. 10-1219682 discloses a representative laser irradiation system for such laser treatment.

For example, in the hair removal field, according to recent statistics of American Society for Aesthetic Plastic Surgery (ASAPS), about 1.2 million treatments have been done on 2012 only in the USA, which has definitely taken first place with treatment frequency of the total beauty field and has taken second place with men.

Laser hair removal has been popular because of demonstrated superiority thereof compared with conventional hair removal in terms of stability and effectiveness as well as enhanced interest of people on beauty.

Laser hair removal is basically based on a principle of 'selective photodermolysis'. The principle is based on the fact that follicles and surrounding tissues have different heat absorptivities due to difference in their pigments. Accordingly, even if a predetermined affected area is irradiated with a laser beam without aiming at each follicle, only follicles may be selectively destroyed.

According to a more recent study, the core mechanism of hair removal using light corresponds to a process for transmitting heat generated from follicles to hair stem cells because hair stem cells that are substantially in charge of growth of hair have no pigment and are attached next to follicles. Accordingly, transmission of an appropriate amount of laser energy to an affected area is a very important factor for hair removal.

When accurate selection of laser intensity fails, side effects such as pigment change, blister, or erythema due to the generation of the excessive amount of blood. On the other hand, transmission of the low amount of laser energy may cause problems, and in this case, treatment effect is degraded and hair growth is also facilitated to cause 'paradoxical hypertrichosis'.

In order to reduce these side effects, a significant amount of research has been conducted to select an optimum laser parameter according to skin color and a position of an affected area.

However, even if appropriate laser intensity is selected, if laser spots are not uniformly distributed, the amounts of laser energies that are actually transmitted to an affected area may be locally different. Frequently, nurses have been entrusted with laser treatment or treatment by half-educated non-practitioners has been prevalently done, and even doctors need to be accustomed to various sizes of new equipment and laser irradiators and various laser parameter settings. Accordingly, in consideration of this, there is high risk due to non-uniform laser transmission.

Accordingly, there is a need to develop simple and effective tools for quantitatively analyzing irradiated laser energy to evaluate proficiency of a laser hair removal operator, but research has not been actively conducted into these tools Most difficulty in manufacturing this system is visualization of an irradiated laser beam.

A hair removal laser uses infrared rays and does not leave prompt vestigium on an irradiation spot.

Recently, a research group has developed a method for calculation of a duplication and omission degree of transmitted energy by analyzing change in heat at a laser irradiation spot using a thermo-graphic camera. However, there are problems in that the thermo-graphic camera is very expensive for daily use and has difficulty in quantitatively recognizing a degree of generated heat when a laser irradiator with a device for cooling an affected area is used or an outdoor temperature is not adjusted because photograph needs to be performed immediately after treatment.

Although other researchers have proposed a visualization method of a laser beam using sensitive paper and a general camera, they observe only a laser profile in one spot in order to recognize irrational characteristics of a laser irradiator.

Although this method is used to recognize proficiency of laser treatment, additional efforts to digitize sensitive paper are required, and it is difficult to reuse the sensitive paper and thus there is a limit for daily use.

Some laser equipments further include a laser installed therein in the form of a laser pointer next to a laser irradiator and emitting lower-power visible rays such that an operator is capable of estimating a position of a laser irradiation p. However, it is difficult to track a process of transmission of a laser beam of total treatment via this method.

SUMMARY OF THE INVENTION

The present invention provides a laser treatment evaluating system for digitizing distribution of a laser irradiation region of laser treatment performed by an operator and providing data so as to facilitate quantitative comparison through the digitized distribution.

The present invention also provides a laser treatment evaluating system for analyzing a laser treatment pattern of an operator, evaluating a laser treatment, and easily evaluating treatment proficiency of the operator or an improving degree of treatment technology so as to use the resulting data as basic data of future treatment training.

According to an aspect of the present invention, a laser treatment evaluating system includes an attenuation unit for attenuating intensity of a laser beam transmitted through a transmissive plate, a camera for photographing the laser beam transmitted through the attenuation unit, and an image data processing apparatus connected to the camera, for processing an image captured by the camera, tracking a trajectory of a laser beam on the transmissive plate, and calculating a distribution state of spots on which the laser beam on the transmissive plate is emitted.

The laser treatment evaluating system may further include a reflection member disposed between the transmissive plate and the attenuation unit, positioned below the transmissive plate, and for converting an irradiation direction of the laser beam transmitted through the transmissive plate toward a side of the attenuation unit.

The laser treatment evaluating system may further include a frame including the transmissive plate disposed thereon and the reflection member obliquely installed therein, wherein the transmissive plate, the reflection member, and the frame constitute a simulation bed.

The attenuation unit may be configured with a polarizing plate or a polarizing film.

The image data processing apparatus may include a signal receiver for receiving an image frame signal transmitted from the camera, a position determiner for determining a position of a centroid of a region with predetermined standard of brightness or more in the image frame, an image synthesizer for positioning a central portion of a template image with a predetermined area on a centroid determined by the position determiner to manufacture a laser distribution map, a calculator for calculating an overlapping and spacing degree between an individual template image indicating a laser irradiation point indicated on the laser distribution map and an adjacent template image and for digitizing a distribution state of the template images, and a controller for controlling operations of the above components.

The laser treatment evaluating system may further include a binarization converter for displaying a region of predetermined standard of brightness or more with first color and converting a region of predetermined standard of brightness or less to second color in the image frame.

According to an aspect of the present invention, a laser treatment evaluating method includes receiving an image frame formed by photographing a laser irradiation point, dividing the received image frame into a first region with predetermined standard of brightness or more and a second region with predetermined standard of brightness or less and processing the first and second regions to be displayed with different colors, and making a laser distribution map with the first region distributed and calculating an overlapping or spacing degree between first regions indicated on the laser distribution map so as to be derived as a digitized result.

The laser treatment evaluating method may further include determining a position of a centroid of the first region, varying according to time flow, generating a template image corresponding to the first region, and positioning a central portion of the generated template image on the centroid of the first region and synthesizing or overlapping the template image and first regions.

The overlapping degree between the first regions may be derived as the digitized result using an overlaying number of times or an overlaying degree between pixels constituting a template image in the first region.

The overlapping degree between the first regions may be derived as the digitized result by recognizing the number of pixels constituting a second region disposed between neighboring and spaced template images.

The laser treatment evaluating method may further include attenuating a laser beam before a laser beam is incident on a camera.

BRIEF DESCRIPTION OF THE DRAWING FIGURES

The above and/or other aspects of the present invention will be more apparent by describing certain exemplary embodiments of the present invention with reference to the accompanying drawings, in which.

Figure 9:
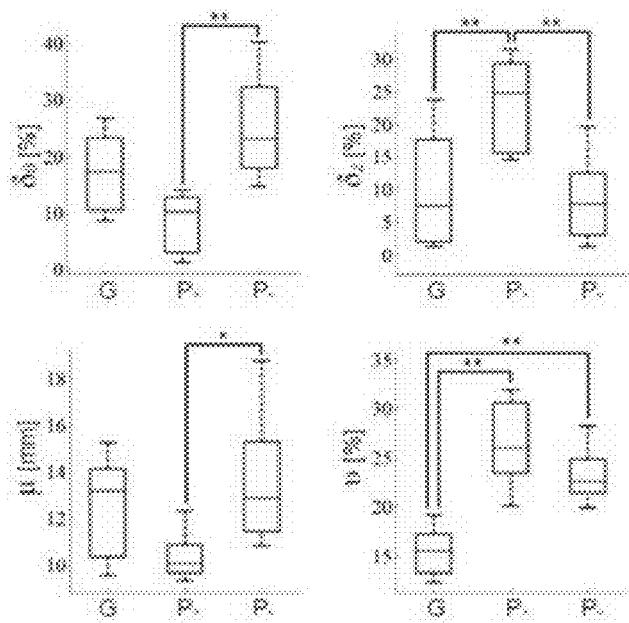
Figure 10:
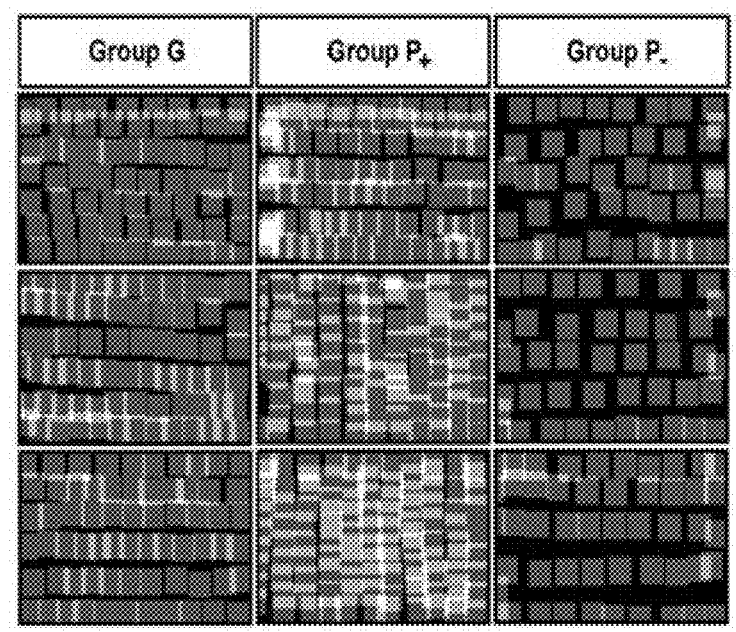

FIG. 9 is a graph for determining effectiveness of a proficiency evaluating parameter between a skilled operator group and an unskilled operator group according to an embodiment of the present invention; and FIG. 10 is a diagram illustrating an LDM indicating laser treatment results performed by a skilled operator group and an unskilled operator group according to an embodiment of the present invention.

DETAILED DESCRIPTION OF THE EXEMPLARY EMBODIMENTS

The attached drawings for illustrating exemplary embodiments of the present invention are referred to in order to gain a sufficient understanding of the present invention, the merits thereof, and the objectives accomplished by the implementation of the present invention.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art.

The terminology used herein is for the purpose of describing particular embodiments and is not intended to limit the invention.

An expression used in the singular encompasses the expression of the plural, unless it has a clearly different meaning in the context.

It will be further understood that the terms "comprises" or "comprising" are not intended to included all elements or all steps described herein, but do not preclude exclusion of some elements or steps described herein or addition of one or more other elements or steps.

Unless otherwise defined, all terms (including technical and scientific terms) used herein have the same meaning as commonly understood by one of ordinary skill in the art to which this invention belongs.

Reference will now be made in detail to the exemplary embodiments of the present invention with reference to the accompanying drawings.

Figure 1:
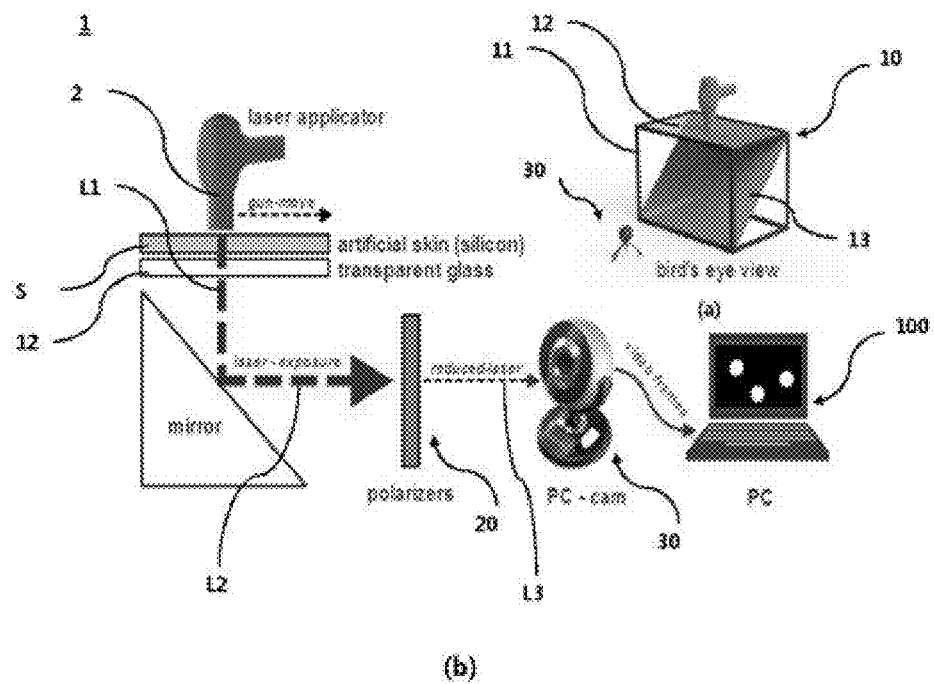
FIG. 1 is a perspective view and schematic side cross-sectional view of a laser treatment evaluating system according to an embodiment of the present invention.

FIG. 1(a) is a perspective view illustrating a state in which a laser treatment evaluating system 1 (hereinafter, referred to as a 'system 1') according to an embodiment of the present invention is applied, and FIG. 1(b) is a schematic side cross-sectional view of the system 1.

As illustrated in FIGS. 1(a) and 1(b), the system 1 according to an embodiment of the present invention includes a simulation bed 10 in which a laser beam L1 emitted from a laser irradiator 2 is incident-reflected-emitted, an attenuation unit 20 for reducing or attenuating intensity of a laser beam L2 transmitted through the simulation bed 10, a camera 30 for photographing a laser beam L3 transmitted through the attenuation unit 20 with remarkably reduced intensity, and an image data processing apparatus 100 connected to the camera 30, which processes image data photographed by the camera 30, tracks a trajectory of the laser beam L1 on the simulation bed 10, and calculates a distribution state of spots on which the laser beam L1 is emitted, as described later.

The simulation bed 10 includes a frame 11 and a transmissive plate 12 disposed on an upper surface of the frame 11.

The transmissive plate 12 is put on an artificial skin S with a predetermined thickness, to which the laser beam L1 is to be emitted during treatment training. The artificial skin S may have a surface formed by copying a state of human skin surface and may be formed of a silicon material.

The artificial skin S may be formed to an appropriate thickness so as to pass the laser beam L1 emitted from the laser irradiator 2 therethrough.

The transmissive plate 12 may be formed of a transparent or translucent material so as to pass the laser beam L1 transmitted through the artificial skin S.

A reflection member 13 such as a mirror may be obliquely disposed below the transmissive plate 12 and may be inclined within the frame 11.

The reflection member 13 reflects the laser beam L1 transmitted through the transmissive plate 12 in a different direction (in a direction toward a camera) from an incident direction.

Accordingly, the simulation bed 10 may include a combination of the frame 11, the transmissive plate 12, and the reflection member 13. However, the transmissive plate 12 or the reflection member 13 may be separable from the frame 11.

The attenuation unit 20 may be disposed between the reflection member 13 and the camera 30.

The attenuation unit 20 may be formed of a polarizing plate or a polarizing film but may be formed of any material for reducing intensity of a laser beam.

Here, the attenuation unit 20 may be formed by overlaying a plurality of polarizing plates or polarizing films.

The attenuation unit 20 is used because a camera 30 used in the present system is a general-purpose personal computer (PC)-camera or camcorder and thus a charge coupled device (CCD) device inside the camera 30 may be damaged when the camera 30 is directly irradiated with a laser beam emitted from the laser irradiator 2.

Although the attenuation unit 20 may be attached to a front surface of a camera lens, any arrangement may be used as long as the attenuation unit 20 is disposed between the camera lens and the reflection member 13.

In any case, the attenuation unit 20 may be disposed to correspond to an emission direction of the reflection member 13 and supported by the frame 11.

The camera 30 may be configured as a PC-camera for detecting visible rays and infrared rays but is not limited to the PC-camera. Accordingly, the camera 30 may be any camera for continuously photographing change in a laser irradiation spot.

The image data processing apparatus 100 is connected to the camera 30, receives and processes an image frame signal acquired from the camera 30, analyzes a distribution state of a spot that is irradiated with the laser beam L1 treated on the artificial skin S, and digitizes and patterns the distribution state.

Data calculated by the image data processing apparatus 100 is quantified and thus is used to facilitate comparison for determining whether a treatment result of an operator is superior or inferior.

Accordingly, improvement according to treatment education for a specific person may be tracked during laser treatment education or training. In addition, it is possible to compare various people.

An experimental embodiment of arrangement of the above components in the present system will be described below.

Table 1 below shows organized specifications of components used in the following experimental embodiment.

TABLE 1

| Devices | Manufacturer | Size | Others |
|---|---|---|---|
| Laser equipment | LightSheer XC, LUMENIS, Inc. | 20 × 20 mm$^2$ (applicator tip) 12 × 12 mm$^2$ (laser window) | Fluence: 10-100 J/cm$^2$ Repetition: 1-2 Hz Wavelength: 800 nm |
| Simulation bed | | 400 × 250 × 250 mm$^2$ | Made of 15 mm × 15 mm aluminum profiles |
| Silicon layer | Anonymous | 400 × 250 mm$^2$ | To mimic the skin friction |
| Glass layer | Anonymous | 400 × 250 mm$^2$ | To mechanically support the silicon layer |
| Mirror | Anonymous | 400 × 350 mm$^2$ | To relect the laser from the top to the front |
| Camera | SPC-A30M, Samsung, Inc | 50 × 50 × 70 mm$^2$ (approx.) | Sensitivity: Visible and infrared regions Frame rate: 30 Hz Resolution: 640 × 480 pixels |
| Polarizers | Visible linear polarizing film, Edmund Optics, Inc. | Six orthogonally aligned 15 × 15 mm$^2$ film cuts | transmission: >40% at 800 nm |

The simulation bed 10 is manufactured using the frame 11 formed of aluminum (Al) with a hexahedron shape. In addition, a glass plate as the transmissive plate 12 is put on an upper surface of the simulation bed 10 and a translucent silicon rubber plate is put on the glass plate in order to copy friction of human skin S.

A reflection mirror as the reflection member 13 is installed at an angle of 45 degrees in the simulation bed 10 in order to reflect forward the laser beam L1 emitted from above the reflection mirror.

The camera 30 is positioned in front of the simulation bed 10 with a distance of 200 mm so as to photograph an entire portion of the reflection member 13 and a direction of the camera 30 is adjusted so as to prevent an image from being distorted.

The attenuation unit 20 is formed by stacking several polarizing plates in the form of film and attached in front of the camera 30, and accordingly, a general camera is used as an infrared camera using the infrared region sensing characteristics of the attenuation unit 20.

By virtue of use of the attenuation unit 20 including a polarizing plate, two additional advantages may be achieved in that incident light is attenuated so as to protect a CCD device of the camera 30 from a high-powered laser beam and images of a visible bandwidth is removed to enhance signal to ratio (SNR) and to facilitate image processing.

Since a laser beam has much higher intensity than visible rays, light is attenuated through the attenuation unit 20 including a polarizing plate such that only laser spots are viewed.

Ideally, the attenuation unit 20 including a pair of vertically-aligned polarizing plates completely blocks light. However, in reality, it is difficult to embody such ideal conditions, and thus six polarizing plates are used in the experimental embodiment.

A contact method of diode laser device is used as the laser irradiator 2 in the experimental embodiment. The device is configured in such a way that a single pulse of laser beam is generated by pushing button installed on the laser irradiator 2 and continuous laser beams are generated at preset speed by maintaining to push the button.

Figure 2:
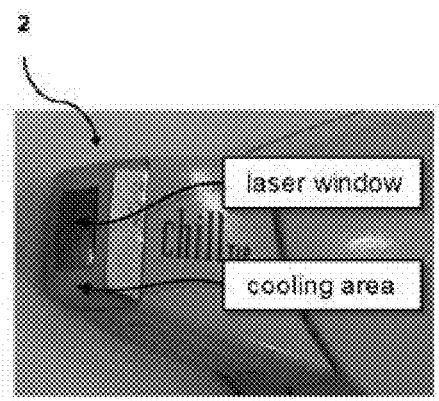
FIG. 2 is an image of a laser irradiator.

The intensity and frequency of irradiated energy are set to 25 J/cm and 2 Hz in order to copy setting that is most commonly and clinically used. As shown in FIG. 2, a cooling area is formed around the laser irradiator 2, and thus an end portion of the laser irradiator 2 is actually larger than a laser window that generates a laser beam.

Figure 3:
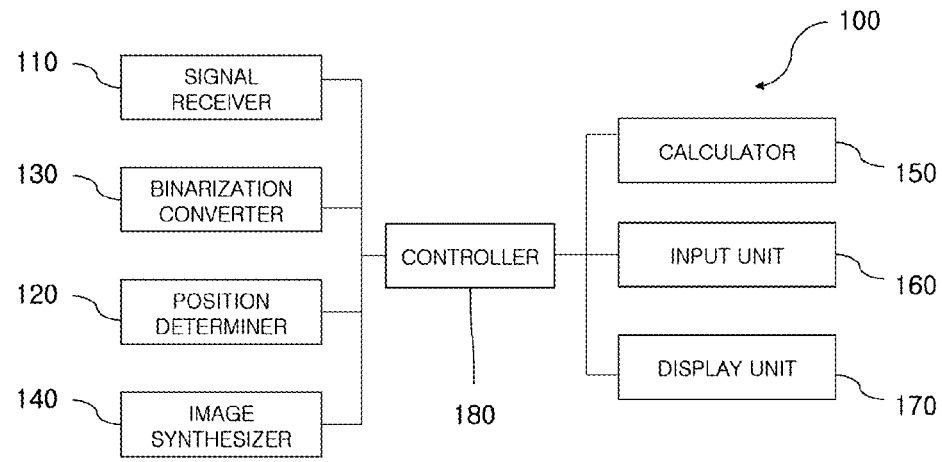
FIG. 3 is a control block diagram of a laser treatment evaluating system according to an embodiment of the present invention.

FIG. 3 is a control block diagram of an image data processing apparatus 100 according to an embodiment of the present invention.

The image data processing apparatus 100 includes a signal receiver 110 for receiving an image frame signal transmitted from a camera, and a position determiner 120 for determining a position of a centroid of a region with predetermined standard of brightness or more in an image frame received by the signal receiver 110.

In addition, the image data processing apparatus 100 also includes a binarization converter 130 for converting color of a region with predetermined standard of brightness or more and color of a region with predetermined standard of brightness or less into white and black, respectively.

The region with predetermined standard of brightness or more may be expressed in the form of approximate circle, oval, or distorted circle (oval).

The predetermined standard may be set but is set to 30% of maximum brightness of an image. However, the predetermined standard may be changed in any way.

The image data processing apparatus 100 also includes an image synthesizer 140 for positioning a central portion of a template image with a predetermined area on a centroid determined by the position determiner 120 to manufacture a laser distribution map.

Although described below, shapes of regions with predetermined standard of brightness or more as initial raw data are different, and thus it is difficult to determine whether adjacent regions are overlaid with each other or a distance between the regions.

Accordingly, it is necessary to equalize the shapes of the regions in order to easily determine an overlaying degree or a distance between the corresponding regions, and in this end, it is necessary to position and overlay or synthesize a template image with a rectangular shape having a similar area to a corresponding region on the corresponding region so as to replace an indicator of a position of the region. This is performed by the image synthesizer 140.

When a separate template image provided by the image synthesizer 140 is positioned in each actual irradiation region, a laser distribution map in which actual laser irradiation regions are indicated is provided.

How much a separate template image indicating a laser irradiation point indicated in the laser distribution map and an adjacent template image are overlaid with each other or spaced apart from each other may be checked with the unaided eye through the laser distribution map.

In addition, the image data processing apparatus 100 may further include a calculator 150 for calculating and digitizing an overlaying and spacing degree of template images, that is, a distribution state of the template images using a predetermined expression to generate data for quantification of the distribution state.

When the image data processing apparatus 100 is a terminal, the image data processing apparatus 100 may further include an input unit 160 such as a keyboard, a mouse, or a touchscreen, and a display unit 170 such as a display that visually displays digitized data or distribution of laser irradiation points as the aforementioned result.

The above components may be controlled by a controller 180 and may be operated in conjunction with each other by the controller 180.

Figure 4:
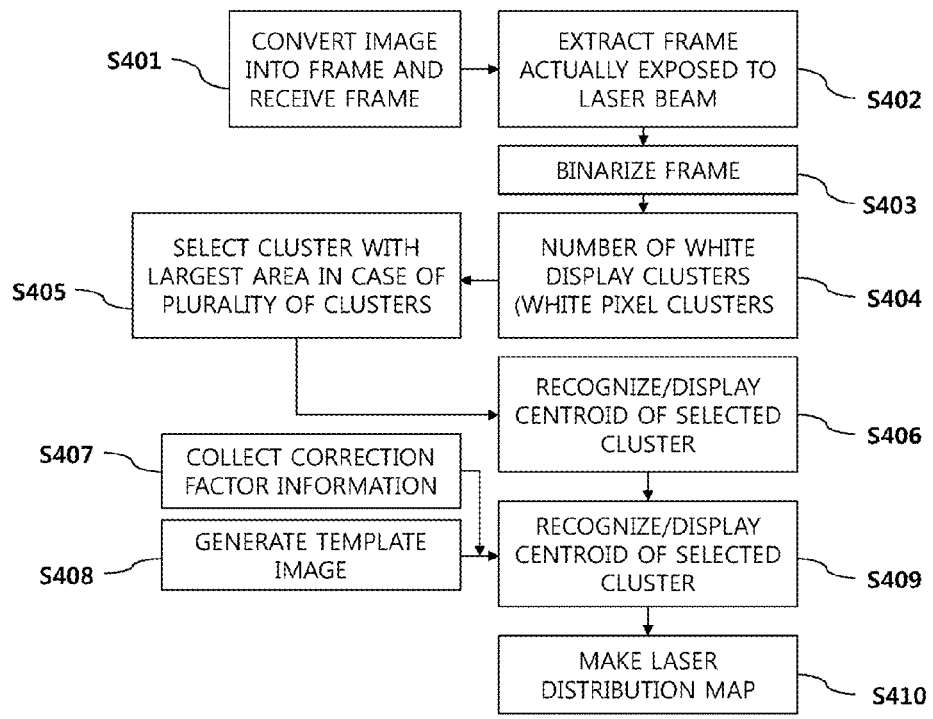
FIG. 4 is a diagram illustrating image processing in a laser treatment evaluating system according to an embodiment of the present invention.

FIG. 4 is a diagram illustrating a procedure for deriving a laser distribution map (LDM) via image processing in the present system.

As shown in FIG. 4, a laser beam that is transmitted through artificial skin and reflected by a reflection member is attenuated in intensity while passing through an attenuation unit such as a polarizing plate.

The laser beam with attenuated intensity is incident on a camera.

When images formed by photographing a trajectory of a laser irradiation point through the camera are converted into frames and the converted frames are received (S401), an image frame indicating an actual laser irradiation point is extracted among the converted frames (S402).

A laser irradiation region that satisfies predetermined standard of brightness (e.g., 30% of maximum brightness) or more is displayed in the image frame.

In addition, when a binarization conversion procedure is performed on the image frame, a region of predetermined brightness or more is displayed with white (or first color) and a region of predetermined brightness or less is displayed with black (or second color) (S403).

In addition, the number of regions (clusters) displayed with white or white pixel clusters and a region (cluster) with a largest area is extracted among the clusters (S404 and S405).

In addition, a centroid of the extracted region (cluster) is retrieved and displayed (S406).

In addition, a correction factor for generation of a template image of a rectangle (or a different shape) corresponding to an area of the white region with the largest area is recognized and the template image is generated (S407 and S408).

When the generated template image is overlaid with each white region (5409), the laser distribution map formed by collecting template images is completed (S410).

Hereinafter, a real case using the present system will be described.

Six novices who have no experience and knowledge about laser treatment are collected and simulate laser treatment on an upper surface of a simulation bed using a laser irradiator.

An operator is permitted to uniformly distribute a laser beam as much as possible on an indicated region between simulation sessions and to put gel on a surface during treatment in order to make the same condition as a real environment.

Safety education is held by an expert prior to the experiment and demonstration of the treatment is given.

Figure 5:
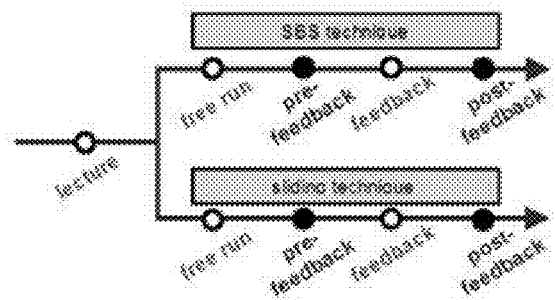
FIG. 5 is a flowchart illustrating a state of overall experiment design according to an embodiment of the present invention.

Operators perform two types of treatments such as SBS technique and sliding technique that are mainly used in a clinical field. The techniques are shown in FIG. 5.

According to the SBS technique, a laser irradiator is repeatedly attached to and detached from an affected area and treatment is performed on an indicated region using a single laser pulse.

According to the sliding technique, a laser irradiator is continuously attached to skin and generated continuous laser pulses and then treatment is performed on an indicated region while the laser irradiator slides on a surface.

Each treatment technique is composed of two sessions that give feedback to each other such that novice operators may achieve training effect. Every simulation session is recorded by the camera 30 positioned next to the simulation bed 10.

First, a correction factor between dimensions in a physical space and an image space is recognized. According to the result represented in an image obtained by perpendicularly positioning the laser irradiator 2 to each edge of a target region indicated by a rectangular shape on the simulation bed 10 and irradiating each edge with a laser pulse 10 times, it is seen that a length of 140 mm in a physical space is expressed to correspond to 397 pixels with fidelity in an image space.

Then an image frame irradiated with a laser pulse is extracted from a moving picture (which corresponds to S402 of FIG. 4).

Figure 6:
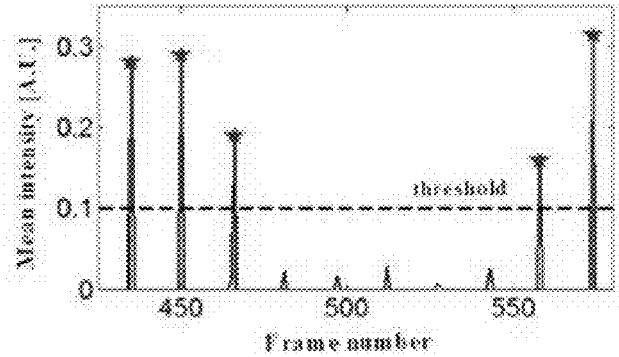
FIG. 6 is a graph showing a reference for dividing a laser irradiation point in a frame irradiated with a laser beam according to an embodiment of the present invention.

Laser pulses are seen as a combination of light pixels in an image, and thus when mean intensity of each frame of a moving picture is shown as FIG. 6, an image frame irradiated with a laser beam exhibits a peak.

Low peaks are occasionally exhibited because an operator emits a laser beam into the air by mistake in the SBS technique, and thus a peak with 30% or less of a highest peak is considered to be invalid.

Figure 7:
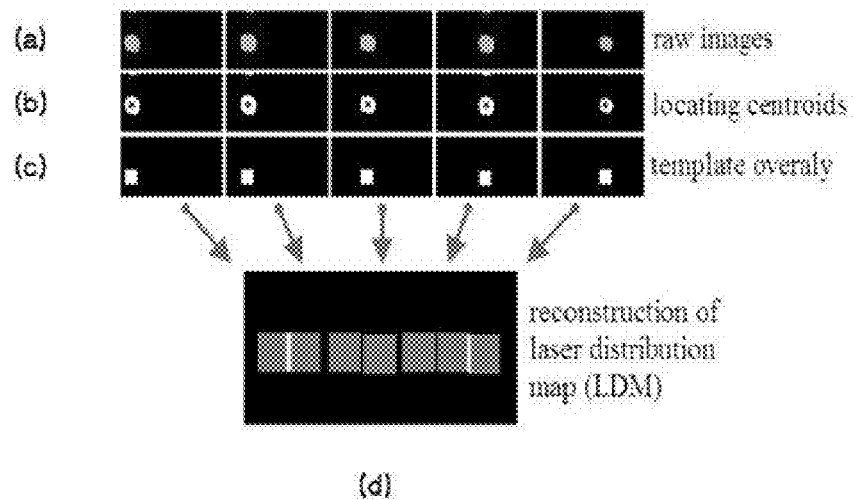
FIG. 7 is an image showing an image processing procedure in a frame irradiated with a laser beam according to an embodiment of the present invention.

Then a coordinate of a laser spot in the frame irradiated with a laser beam is obtained (refer to FIG. 7).

To this end, first, an image is binarized to black and white using a threshold corresponding to 30% of maximum intensity and a centram point of white clusters is calculated (which corresponds to S403 of FIG. 4).

Usually, a binarized image has only one white cluster, but in some cases, a plurality of white clusters are seen because a laser beam reflected by a frame (which is formed of aluminum) of the simulation bed 10 is reflected, and in this case, a white cluster with a largest area is considered to be an actual laser spot.

Lastly, a template image representing the actual shape and size of the laser spot is positioned on a centroid of the laser spot known in the previous operation (refer to FIG. 7). In the present operation, all pixel values in the template image are regularly set to 1 (which corresponds to S408 to 409 of FIG. 4).

FIG. 7(*a*) illustrates a combination of image frames, which represents change in position of laser irradiation point (spot) according to time. Kinds of pictures of momentary positions are arranged in a time sequence (raw data).

FIG. 7(*b*) illustrates a centroid of a laser irradiation point (spot) in each image frame and FIG. 7(*c*) illustrates image frames synthesized or overlaid by positioning a generated template image on a centroid of a laser irradiation point (spot) of each image frame.

In addition, FIG. 7(*d*) is obtained by positioning template images on the plurality of image frames shown in FIG. 7(*c*) in one image frame.

That is, a plurality of pictures indicating position change is synthesized into one sheet so as to easily recognize position change according to time.

This series of image reconstruction procedures are required because laser spots in an image are displayed to be spread unlike an actual shape due to influence of a silicon sheet positioned on a simulation bed and the point spread characteristic of a camera.

Based on the correction factor between the dimensions, recognized in the first operation of image processing, the present experimental embodiment uses a template image with a square shape of 34 by 34 pixels.

The laser distribution map (LDM) is reconstructed by overlaying laser spots indicated by the template images.

With regard to reconstruction, the LDM may have all initial values of 0 and have the number corresponding to an overlaying number of times in an overlaid point.

For quantitative analysis of the LDM derived from the present system, four performance indexes are developed.

First two indexes $\delta_0$ and $\delta_z$ are used to measure errors, indicate percentage of an area in which laser irradiation is not performed with respect to an area of a display region and percentage of an area in which laser irradiation is repeatedly performed, respectively, and are defined according to Expressions 1 and 2 below.

$$\delta_0[\%] = \frac{(A_0 - A_1)}{A_0} \times 100 \quad \text{[Expression 1]}$$

$$\delta_2[\%] = \frac{\sum_{k=2}^{n} A_k}{A_0} \times 100 \quad \text{[Expression 2]}$$

Here, $$A_k = \sum_{m=1}^{M} \sum_{n=1}^{N} L(m, n) \circ k \quad \text{[Expression 3]}$$

$$k = 1, 2, \ldots, \alpha$$

and $$A_0 = M \times N$$

$$x \circ y = \begin{cases} 1, & \text{if } x \geq y \\ 0, & \text{otherwise} \end{cases} \quad \text{[Expression 4]}$$

Here, α is a highest pixel value in a laser distribution map (LDM) indicated by L(m, n), that is, a maximum number of duplication times in the corresponding LDM, and M and N indicate sizes (horizontal and vertical sizes) of an image in pixel units.

Since duplication may occur to exceed 2 times in one point, it is noted that a maximum value of $\delta_z$ may exceed 100% (that is, since $A_k$ of a laser beam is added, a multiple overlaying degree is counted).

μ shows an estimate of an operator for a laser spot size and is defined as an mean value of a distance $d_c$ of centroids of two consecutive laser spots according to Expression 5 below.

$$\mu[mm] = \text{mean}(d_c) \times C \quad \text{[Expression 5]}$$

Here, $$d_c = \{x_i | x_i = |S(i) - S(i+1)|, i=1, 2, \ldots, (\beta-1)\} \quad \text{[Expression 6]}$$

A constant C is a correction factor for connection between dimensions in a physical space and an image space and used as 0.35 mm/pixel in the present experimental embodiment.

S indicates arrangement indicating coordinates of a centroid of a laser spot and β is the number of laser spots applied to a display region. When laser beams are ideally distributed, μ may be equal to the size (here, 12 mm) of a window from which a laser beam is actually emitted.

ν is an index indicating randomness of the LDM and is defined by obtaining distance values between each laser spot and another laser spot with a shortest distance from the corresponding laser spot and normalizing variance values of the distance values according to Expression 7 below.

$$0[\%] = \frac{std(d_0)}{\text{mean}(d_0)} \times 100 \quad \text{[Expression 7]}$$

Here, $$d_n = \{y_i | y_i = \min(|S(i) - s(j)|), \forall j \in \{1, 2, \ldots, \beta\}\} \quad \text{[Expression 8]}$$

It is noted that increase in ν may cause increase in both or one of $\delta_0$ and $\delta_z$ but converse is not satisfied.

Figure 8:
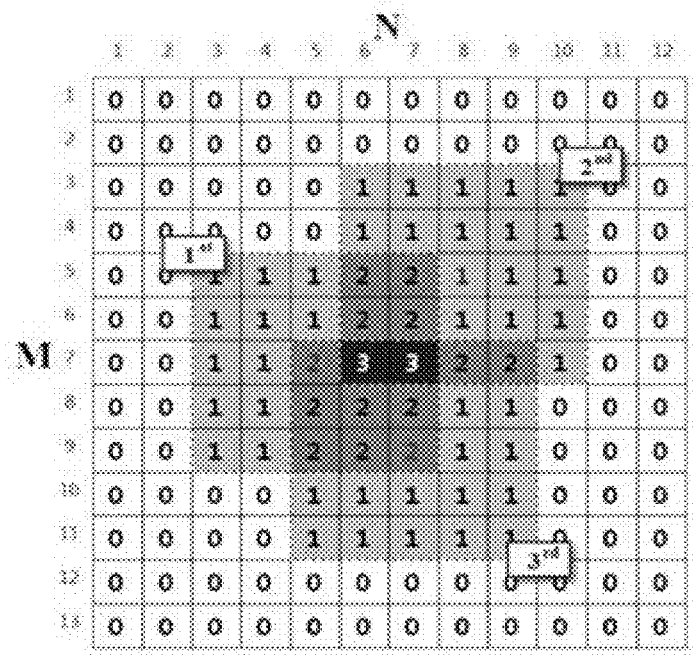
FIG. 8 is a diagram illustrating a laser distribution map (LDM) for quantifying an overlaying state between three arbitrary laser irradiation points according to an embodiment of the present invention.

In order to exemplify a process of calculating proficiency factors, a laser distribution map (LDM) artificially synthesized with three laser spots is shown in FIG. 8.

In this example, the size of the LDM and the size of a laser spot are set to 13×12 and 5×5 pixels, respectively, and a correction factor C is set to 1 (i.e., 1 mm=1 pixel).

The number written in a position of a pixel refers to a number of times of irradiating each point with a laser beam, and a centroid of a laser spot is indicated to be red. The proficiency factors are calculated as follows.

1. A maximum number of duplication times α=3.
2. $A_0, A_1, A_2$, and $A_3$ are 156, 58, 15, and 2, respectively according to Expression 3 above.
3. $\delta_0$=62.82% and $\delta_z$=10.90% according to Expressions 1 and 2 above.
4. S={(7, 5), (5, 8), (9, 7)}.
5. $d_c$={3.61, 4.12} and $d_n$={2.83, 3.61, 2.83} according to Expressions 6 and 8 above
6. μ=3.87 mm and ν=0.15% according to Expressions 5 and 7.

A comparison result in terms of statistics is as follows.

Total of 24 laser distribution maps (LDMs) (six operators, two types of different treatments, and before/after training) are collected and statistically processed.

Table 2 below shows classification of collected data.

TABLE 2

| SBS technique | | Sliding technique | |
|---|---|---|---|
| Prefeedback D1 | Postfeedback D2 | Prefeedback D3 | Postfeedback D4 |

In order to evaluate utility of proposed laser treatment evaluation of proficiency factors, a laser distribution map (LDM) collected by a skilled dermatologist is classified into total of three proficiency groups.

First, eight LDMs with best proficiency are collected and are referred to as Group G.

The other 16 LDMs exhibit relatively low proficiency. In this regard, there are two different reasons for degraded proficiency, and thus the 16 LDMs are classified into Groups P+ and P−.

Accordingly, eight LDMs with an excessive duplication degree are classified as Group P+ and, on the other hand, the eight LDMs with an excessive omission degree are classified as Group P−.

Training effects are checked by comparing data before training and data before training, and in detail, by comparing D1 and D2 in the SBS technique and comparing D3 and D4 in the sliding technique.

In the present experimental embodiment, since it is assumed that training effects are different between treatment methods, in this end, D1 is compared with D3 (before training) and D2 is compared with D4 (after training).

The comparison result is as follows.

As the analysis result using an analysis of variance (ANOVA) statistics scheme, mean values of proficiency factors are highly different according to proficiency groups (refer to FIG. 9).

Group G exhibits a low value in terms of $\delta_z$ and ν compared with Group P+ and also exhibits low value in terms of ν compared with Group P. Groups P+ and P− are also differentiated based on any single proficiency factor other than ν.

It is seen that, as a result of a single sample t-test statistics scheme, only Group P+ is significantly different from μ of 12 mm (Refer to Table 3 below).

TABLE 3

| | μ: 12 mm (mean ± SD) | P |
|---|---|---|
| Group G | +0.50 ± 2.17 | 0.537 |
| Group P+ | −1.65 P2.1 | 0.002** |
| Group P− | 1.59 ± 2.74 | 0.144 |

*P < 0.05,
**P < 0.01
Negative value indicates shorter spacing between consecutive laser spots In order to exemplify a proficiency difference, nine LDMs selected from the three proficiency groups are shown in FIG. 10.

It may be seen that Group G forms more satisfactory laser distribution than the other two groups. In detail, Groups P+ and P− exhibit a higher number of duplication and omission times than Group G. In this example, $\delta_z$ is exhibited as 29.08 in Group P+ and is exhibited as 6.05 in Group G.

$\delta_o$ is exhibited as 23.77 in Group P− and is exhibited as 13.12 in Group G. Accordingly, quantitative analysis via a proficiency factor coincide qualitative analysis with the naked eyes.

Prefeedback data and postfeedback data are compared in the data classification described with reference to Table 2 above so as to check training effects.

Mean values shown in Table 4 below indicate a difference between D1 and D2 in the sliding technique and a difference between D3 and D4 in the SBS technique.

TABLE 4

| | Sliding mode (mean ± SD) | P | SBS mode (mean ± SD) | P |
|---|---|---|---|---|
| $\delta_z$[%] | +6.00 ± 8.03 | 0.127 | +1.07 ± 5.27 | 0.641 |
| $\delta_o$[%] | −6.32 ± 5.12 | 0.029* | −4.68 ± 6.14 | 0.121 |

TABLE 4-continued

|  | Sliding mode (mean ± SD) | P | SBS mode (mean ± SD) | P |
|---|---|---|---|---|
| μ[mm] | −1.79 ± 1.67 | 0.047* | −0.32 ± 1.08 | 0.504 |
| υ [%] | −0.77 ± 3.83 | 0.645 | +0.75 ± 1.22 | 0.188 |

Prefeedback μ values were >12 mm, regardless of techniques
(13.49 in sliding, and 13.86 in SBS)
Positive signs indicate a higher index value in postfeedback session
*P < 0.05,
**P < 0.01

As a test result of corresponding sample t, it is seen that feedback is effective only in the sliding technique and factor values $\delta_O$ and μ are significantly reduced.

M is reduced to 11.70 mm from 13.49 mm and is close to 12 mm as an ideal value. $\delta_z$ tends to be increased but a degree thereof is not statically significant.

Compared with the sliding technique, any proficiency factor is not significantly changed in the SBS technique. For reference, values shown in Table 4 above are obtained by subtracting a value before training from a value after training.

A difference between treatment methods is checked by comparing D1 and D3 before training and is checked by comparing D2 and D4 after training, and this result is summarized in Table 5 below.

TABLE 5

|  | Before training (mean ± SD) | P | After training (mean ± SD) | P |
|---|---|---|---|---|
| $\delta_z$[%] | −2.87 ± 8.50 | 0.445 | +2.06 ± 12.80 | 0.710 |
| $\delta_o$[%] | +5.40 ± 6.78 | 0.108 | +3.76 ± 13.31 | 0.520 |
| μ[mm] | +1.63 ± 1.58 | 0.053 | +0.16 ± 1.45 | 0.794 |
| υ [%] | +7.21 ± 5.79 | 0.028* | +5.69 ± 5.79 | 0.146 |

Positive signs indicate higher index values in the sliding technique
*P < 0.05,
**P < 0.01

In the before training session, operators exhibit much higher υ in the sliding technique than in the SBS technique and do not exhibit any difference in the remaining factors between the treatment methods. For reference, values are calculated based on the SBS technique.

It is very important to uniformly transmit laser energy in laser treatment for stable and effective treatment.

The embodiments of the present invention propose an inexpensive and easily operated system that may visualize and analyze simulated laser patterns in a preclinical environment without an expensive infrared system.

Four proficiency evaluation factors for evaluation of proficiency of laser treatment for analysis are developed and utility of the factors is also checked.

In addition, it is seen that the developed system may be applied to operator training to reduce omission error of 6.32% and to maintain a more accurate interval between laser spots and it is sufficiently seen that the system may also be used as a scientific tool for checking a difference between the SBS technique and the sliding technique.

Although the aforementioned experimental embodiment of the present invention is implemented by copying a laser hair removal environment, a treatment pattern quantification scheme proposed according to the experimental embodiment may also be applied in the same way to other aesthetic laser treatment fields by slightly correcting the algorithm.

For example, omission and duplication degrees of a laser beam need to be differently reflected according to a type of target disorder (hair, blood vessel, wrinkle, pimple, etc.) and even if the same disorder is treated, the characteristic of a laser beam may vary according to a type of a used device.

In this case, when different weights may be applied to an evaluation factor indicating duplication or omission to evaluate the quality of treatment and a template image may be corrected so as to copy the characteristic of a laser beam of the used device, the scheme proposed by the embodiments of the present invention may be used irrespective of change in treatment or device type.

According to the embodiments of the present invention, it is advantageous to quantitatively evaluate a laser treatment result. In particular, it is advantageous to configure a treatment proficiency evaluation system with low costs by tracking movement of a trajectory of a laser irradiation point using a general camera without an expensive thermo-graphic camera.

Laser irradiation spots in an image frame are collected or spread, and thus difficulty in quantification of an overlaying and spacing degree between the laser irradiation spots is overcome by introducing the scheme of overlaying or synthesizing template images.

In particular, it is advantageous to quantify and easily evaluate proficiency of treatment by digitizing an overlaying number of times or overlaying degree between pixels constituting a template image or digitizing an interval between spaced template images using the number of pixels of a region in which a template image is not position.

It is advantageous to easily evaluate whether proficiency is improved according to training of a specific operator and to easily compare proficiency between operators via the system.

The foregoing exemplary embodiments and advantages are merely exemplary and are not to be construed as limiting the present invention. Also, the description of the exemplary embodiments of the present invention is intended to be illustrative, and not to limit the scope of the claims, and many alternatives, modifications, and variations will be apparent to those skilled in the art.

What is claimed is:

1. A laser treatment evaluating system comprising:
   an attenuation unit for attenuating intensity of a laser beam transmitted through a transmissive plate;
   a camera for photographing the laser beam transmitted through the attenuation unit; and
   an image data processing apparatus connected to the camera, for processing an image captured by the camera, tracking a trajectory of a laser beam on the transmissive plate, and calculating a distribution state of spots on which the laser beam on the transmissive plate is emitted,
   wherein the image data processing apparatus comprises:
      a signal receiver for receiving an image frame signal transmitted from the camera;
      a position determiner for determining a position of a centroid of a region with predetermined standard of brightness or more in the image frame;
      an image synthesizer for positioning a central portion of a template image with a predetermined area on a centroid determined by the position determiner to manufacture a laser distribution map;
      a calculator for calculating an overlapping and spacing degree between an individual template image indicating a laser irradiation point indicated on the laser distribution map and an adjacent template image and for digitizing a distribution state of the template images; and a controller for controlling operations of the above components.

2. The laser treatment evaluating system according to claim 1, further comprising a reflection member disposed between the transmissive plate and the attenuation unit, positioned below the transmissive plate, and for converting an irradiation direction of the laser beam transmitted through the transmissive plate toward a side of the attenuation unit.

3. The laser treatment evaluating system according to claim 2, further comprising a frame comprising the transmissive plate disposed thereon and the reflection member obliquely installed therein,
   wherein the transmissive plate, the reflection member, and the frame constitute a simulation bed.

4. The laser treatment evaluating system according to claim 1, wherein the attenuation unit is configured with a polarizing plate or a polarizing film.

5. The laser treatment evaluating system according to claim 1, further comprising a binarization converter for displaying a region of predetermined standard of brightness or more with first color and converting a region of predetermined standard of brightness or less to second color in the image frame.

6. A laser treatment evaluating method comprising:
   receiving an image frame formed by photographing a laser irradiation point;
   dividing the received image frame into a first region with predetermined standard of brightness or more and a second region with predetermined standard of brightness or less and processing the first and second regions to be displayed with different colors; and
   making a laser distribution map with the first region distributed and calculating an overlapping or spacing degree between first regions indicated on the laser distribution map so as to be derived as a digitized result.

7. The laser treatment evaluating method according to claim 6, further comprising:
   determining a position of a centroid of the first region, varying according to time flow;
   generating a template image corresponding to the first region; and
   positioning a central portion of the generated template image on the centroid of the first region and synthesizing or overlapping the template image and first regions.

8. The laser treatment evaluating method according to claim 7, wherein the overlapping degree between the first regions is derived as the digitized result using an overlaying number of times or an overlaying degree between pixels constituting a template image in the first region.

9. The laser treatment evaluating method according to claim 7, wherein the overlapping degree between the first regions is derived as the digitized result by recognizing the number of pixels constituting a second region disposed between neighboring and spaced template images.

10. The laser treatment evaluating method according to claim 6, further comprising attenuating a laser beam before a laser beam is incident on a camera.

* * * * *